US010967131B2

(12) United States Patent
Schildt et al.

(10) Patent No.: US 10,967,131 B2
(45) Date of Patent: *Apr. 6, 2021

(54) ASSEMBLY TO ADMINISTER INSULIN FROM A CARTRIDGE

(71) Applicant: EMPERRA GMBH E-HEALTH TECHNOLOGIES, Potsdam (DE)

(72) Inventors: Janko Schildt, Potsdam (DE); Florian Ruehle, Potsdam (DE)

(73) Assignee: EMPERRA GMBH E-HEALTH TECHNOLOGIES, Potsdam (DE)

( * ) Notice: Subject to any disclaimer, the term of this patent is extended or adjusted under 35 U.S.C. 154(b) by 214 days.

This patent is subject to a terminal disclaimer.

(21) Appl. No.: 15/954,833

(22) Filed: Apr. 17, 2018

(65) Prior Publication Data

US 2018/0228979 A1 Aug. 16, 2018

Related U.S. Application Data

(63) Continuation of application No. 13/246,640, filed on Sep. 27, 2011, now Pat. No. 10,010,678, which is a (Continued)

(51) Int. Cl.
*A61M 5/315* (2006.01)
*A61M 5/24* (2006.01)
(Continued)

(52) U.S. Cl.
CPC .......... *A61M 5/31525* (2013.01); *A61M 5/24* (2013.01); *A61M 5/3129* (2013.01); *A61M 5/31553* (2013.01); *A61M 5/31563* (2013.01); *A61M 5/31571* (2013.01); *A61M 2005/2407* (2013.01); *A61M 2205/3317* (2013.01); *A61M 2205/3592* (2013.01); *A61M 2205/52* (2013.01); *A61M 2205/581* (2013.01);
(Continued)

(58) Field of Classification Search
None
See application file for complete search history.

(56) References Cited

U.S. PATENT DOCUMENTS 5,308,340 A 5/1994 Harris
5,925,021 A 7/1999 Castellano et al.
(Continued)

FOREIGN PATENT DOCUMENTS

DE 29918149 U1 12/1999
DE 10051576 A1 2/2002
(Continued)

*Primary Examiner* — Nathan R Price
*Assistant Examiner* — Weng Lee
(74) *Attorney, Agent, or Firm* — Fox Rothschild LLP

(57) ABSTRACT

An assembly for the administration of a selected dosage of insulin or other medicaments from a cartridge by moving a plug guided in said cartridge, comprises an adapter assembly for adapting cartridges with different dimensions or contents. The adapter assembly comprises a first threaded element threaded with a thread lead and movable in a moving direction to move the plug, and a second threaded element threaded with a thread lead for setting a selected dosage, pivotably screwed to said first threaded element and limiting the movement of said first threaded element, and wherein said thread lead of said first element and said thread lead of said second threaded element are adapted to the dimensions and/or the contents of said cartridge.

2 Claims, 14 Drawing Sheets

Related U.S. Application Data continuation of application No. PCT/EP2010/054383, filed on Mar. 31, 2010.

(51) Int. Cl.
    *A61M 5/31*     (2006.01)
    *G16H 20/10*     (2018.01)
    *G16H 20/17*     (2018.01)

(52) U.S. Cl.
    CPC ..... *A61M 2205/8212* (2013.01); *G16H 20/10* (2018.01); *G16H 20/17* (2018.01)

(56) References Cited

U.S. PATENT DOCUMENTS

| | | |
|---|---|---|
| 6,277,099 B1 | 8/2001 | Strowe et al. |
| 6,585,698 B1 | 7/2003 | Packman et al. |
| 7,427,275 B2 | 9/2008 | DeRuntz et al. |
| 2002/0143288 A1 | 10/2002 | Larsen et al. |
| 2005/0049655 A1 | 3/2005 | Boveja et al. |
| 2006/0175427 A1 | 8/2006 | Jonientz et al. |
| 2008/0281275 A1 | 11/2008 | Moller |
| 2009/0209920 A1 | 8/2009 | Moller et al. |
| 2012/0029443 A1 | 2/2012 | Holmqvist |

FOREIGN PATENT DOCUMENTS

| | | |
|---|---|---|
| DE | 10147973 A1 | 4/2003 |
| DE | 10207057 A1 | 8/2003 |
| DE | 102005018305 A1 | 12/2005 |
| EP | 1095668 A1 | 5/2001 |
| WO | 93/10839 A1 | 6/1993 |
| WO | 97/17095 A1 | 5/1997 |
| WO | 98/42394 A1 | 10/1998 |

ASSEMBLY TO ADMINISTER INSULIN FROM A CARTRIDGE

CROSS-REFERENCE TO RELATED APPLICATIONS

This patent application is a continuation of U.S. application Ser. No. 13/246,640 filed on Sep. 27, 2011, which is a continuation of and claims priority to PCT application PCT/EP2010/054383, with an international filing date of Mar. 31, 2010 and a Convention priority date of 1 Apr. 2009. The contents of which are all hereby incorporated in their entireties herein.

STATEMENT REGARDING FEDERALLY-SPONSORED RESEARCH OR DEVELOPMENT

Not applicable.

TECHNICAL FIELD

The invention relates to an assembly to administer a selected dosage of insulin or other medicaments from a cartridge by feed movement of a plug movably guided in the cartridge.

BACKGROUND OF THE INVENTION

Such application assemblies are particularly employed in insulin therapy for diabetes mellitus. In insulin therapy, particularly in the intensified insulin therapy and conventional insulin therapy, insulin is not applied in constant amounts. In conventional insulin therapy insulin is applied at pre-scheduled times. The daily routine of a patient complies with such times. In intensified conventional insulin therapy a basal requirement of insulin is provided, often by a slow acting and long lasting insulin, the basal insulin. At meals, a fast-acting insulin is applied. The dosage of the fast-acting insulin is essentially based on the comprised carbohydrates. The dosage is hence specifically chosen depending on external circumstances. Such circumstances are, for example, the time of the day, the amount of exercise, the diet and the like.

Diabetes mellitus can have severe long-term consequences and impairment of the body. They can be considerably reduced by means of an adapted insulin therapy, preferably an intensified conventional insulin therapy. A wrong dosage can also have short term effects like hypoglycemia. An optimal adjustment of the dosage to the respective circumstances is, therefore, highly desirable.

For this reason diabetes mellitus patients are urged to take minutes of their lifestyle and applied doses of insulin. The record keeping is time consuming. The record usually comprises the measured blood sugar level, the consumed amount of carbohydrates, the applied dosage of insulin as well as time and date. The attending physician or the patient can determine or adjust the respective dosage using this record.

The administration of insulin is carried out with an injection aid (also known as pen), that is provided with an injection needle and a cartridge containing the medicament or with an insulin pump with a cartridge. The insulin pump is employed continuously whereas a pen is employed for single application procedures.

Known pens externally resemble a large ball pen. They comprise a housing and a cartridge. Cartridge is understood to be a cylindrical ampoule having a puncturable membrane on one side. The other side is closed by a movable plug. The medicament is contained in the cartridge. The cartridge is usually exchangeable. However, assemblies are known that are provided as disposable pens. Cartridges, their content, dimensions and their handling are not standardized. Therefore, a cartridge of one manufacturer can normally not be inserted into a pen of another manufacturer.

A pen comprises a measuring device. The required dosage is adjusted with a dose setting knob. It is then applied into the hypodermic fat tissue. Some pens display the adjusted dosage on a display with electrical energy instead of a mechanical display. The display is driven by a coin cell. The patient can adjust the dosage and note it down in the record. The diabetes log is shown to a physician. The physician can work out the further therapy together with further body parameters i.e. blood sugar values, body measurements and blood pressure.

Keeping records according to known methods is time consuming. It can lead to carelessness of the patient. There is a danger of knowingly or unknowingly wrong recording of the insulin dosage. This can, for example, occur if the patient acts contrary to the physician's instructions. The patient usually does not like to disclose a faulty self medication. Hence, the data on the record and the adaption of the prospective therapy will be wrong. The patient will suffer severe acute or long term consequences.

DE 101 47 973 A1 discloses an assembly where sensors are provided for the detection of the kind of cartridge in order to prevent mistakes. For this purpose, sensors are attached to the assembly, which interact with cognitional elements on a cartridge. Thereby, the medicament in a cartridge unambiguously read out.

DE 10 2005 018 305 A1 discloses an application assembly, where a dosage application knob is secured against accidental actuation. An adjustment ring is provided on one end of the application assembly for adjustment of a dosage. The dosage application knob is positioned separate from the adjustment ring and only serves for the application of an adjusted dosage. The applied dosage can be adjusted with the adjustment ring. The actuator is glidingly held in the adjustment ring. By rotating the adjustment ring the dosage application knob is displaced in axial direction. The actuator never rises beyond the adjustment ring. This serves as securing means to prevent that the dose is accidentally actuated.

In the prior art it is disadvantageous that the patient must use different pens for insulin of different manufacturers. This forces the patient to learn a new handling. Furthermore, it is disadvantageous that different insulin pens are provided with different security mechanisms to prevent accidental activation.

BRIEF SUMMARY OF THE INVENTION

It is an object of the invention to provide an assembly of the aforementioned kind that is more cost effective an easier to handle. It is a further object of the invention to provide an assembly with a more secure handling.

According to the present invention this object is achieved with an application assembly of the aforementioned kind by
(a) an adapter assembly to adapt cartridges with different dimensions or contents, comprising
(b) a first threaded element movable in a moving direction to move the plug, and
(c) a second threaded element for adjusting a selected dosage, pivotably screwed to the first threaded element and limiting the movement of the first threaded element, wherein (d) the thread lead of the first and the second threaded element is adapted to the dimensions and/or the contents of the cartridge.

Insulins of different suppliers are offered in different cartridge sizes. An assembly according to the invention enables the user to use the same pen for insulins of different suppliers. This reduces the purchase costs, because there is no need to buy a new pen upon change of the medicament. The user has the advantage that he does not need to get used to the handling of a new application assembly. The handling is, therefore, facilitated and more secure.

Cartridges provided by different suppliers may have different outer dimensions. Hence, a cartridge of a different supplier can usually not be inserted into the pen known in the art. An adapter assembly will compensate such drawbacks. Cartridges provided by different suppliers may be used. The flank lead of the threaded elements defines the feed movement of the plug. Thereby, it is ensured that the applied dosage does not depend on the shape of the cartridge. An individual specific flank lead is assigned to each kind of cartridge.

The invention is based on the finding that the integration of threaded elements with matching flank leads allows the use of different cartridges. The cartridges may have different dimensions and contents. Accordingly, the feed movement of the plug is different for different cartridges.

Preferably, the assembly comprises a pivotable dose setting knob and means for transferring the rotational movement of the dose setting knob to the second threaded element. In particular, the dose setting knob may be locked. In a particularly preferred embodiment of the present invention a housing is provided, the dose setting knob adapted to be pressed inside against the force of a pressure spring in the housing and which dose setting knob is adapted to be releasably locked therein. The dose setting knob operates similarly to the mechanics of a ball pen. In order to use the assembly the dose setting knob is released and is pushed outside by the spring. It may then be rotated in the desired way. The dose is selected by rotation. The rotational movement is transmitted to the threaded element. In order to administer the medicament the dose setting knob is pushed. If the assembly is not used the dose setting knob is pressed inside and secured against accidental actuation.

According to a modification of the invention it is provided, that (a) the first threaded element is formed by a threaded rod with an external, male thread, (b) the adapter assembly comprises a casing having an open side for receiving a cartridge and which is provided with an aperture at its opposite end for guiding the threaded rod in a rotationally secured way, and (c) the second threaded element is formed by a nut, screwed on the threaded rod from the outside of the casing, the axial position of which is selected by rotation.

The production of such an assembly is cost effective and the design is simple. It is understand that it is possible to use a threaded hollow shaft or the like. Any other securing means may be used instead of a casing for an adapter.

Preferably, securing means may be provided to block a movement of the threaded rod in an opposite movement direction.

The securing means ensure that the adapter may be used only once. With the securing means the threaded element cannot be returned to the starting position. Once insulin has been applied no new cartridge can be inserted. The adapter needs to be replaced. The mechanical wear and tear of the components is reduced because the adapter can only be used once. The application assembly works more precise and more reliable.

Preferably, the securing means are formed by a securing disk attached to the threaded rod inside the casing which is locked by the cartridge.

The securing means can be formed by a disk attached to the threaded rod with an opening between the front end of the cartridge and the inner front end of the casing and having flexible tongues in the range of the opening engaging with the thread of the threaded rod.

Such a securing disk is cost effective in production and reliable in handling. It is understood that the securing means can also be provided at the casing.

In a preferred embodiment of the invention a sensor assembly is provided for contactless registration of the applied dosage. By not using mechanical parts wear and tear is reduced and therefore, the reliability of the application assembly is improved. The sensor assembly may contain:

(a) magnets on one of the rotating components for adjusting the dosage, (b) magnetic sensors detecting the rotation of the magnets, and (c) processing, and display means for processing and/or displaying a dosage corresponding to the detected movement determined from the detected rotation.

Magnets are well suited for the contactless transmission of signals, because magnetic fields are spatially extended. Sensors can detect magnetic fields without being in mechanic contact to the magnets. The magnetic fields of magnets remain constant over a long period of time, thus the reliability of the application assembly is improved.

Preferably, means are provided for determining and registering the time and/or the date and means for determining and registering the selected and administered dosage. By saving the date and/or the time together with the adjusted dosage the patient can easily monitor when he applied insulin for the last time. For basal insulin it is important to meet exact application times of insulin. This is realized by the indication of the elapsed time since the last administered dosage. With such an arrangement the patient can control when he administered the last dosage. This is helpful if the patient wants to control the development of the blood sugar values since the last dosage of insulin. Furthermore, the selected dosage of insulin can be saved. The patient can then reconstruct if the applied dosage was correctly calculated.

The date and/or the time may be transmitted to a receiver by means of a transmitter together with the signal of the applied amount of the medicament. The data may also be recorded and transmitted independently.

In order to reduce the transmission distance the signal can be transmitted to, for example, a cell phone by a short range broadcast standard (such as, for example, Bluetooth®). The further transmission can then be effected by a common mobile telephone network. It is understood that any other transmission is also possible. Thus, the information may also be transmitted to a receiver which is connected to the internet. Also, GSM and the like are suited for the transmission of the signal. The transmitted data may be encrypted.

The assembly can also be provided with a receiver for receiving data. Thereby, notices of receipt, warnings or any other data can be received. In particular, an assembly with a receiver enables the communication with the physician in charge even if another communication is not possible.

The assembly may be provided with a display for showing warnings, transmission data, status information and the like. This facilitates the handling.

Furthermore, the assembly may be provided with means for acoustic in- and/or output of data. During the course of the disease impaired vision can occur for diabetics. The use of an acoustic in- and/or output of data ensures that even these patients can handle an injection aid.

The assembly may be provided with a touch pad for the in- and output of data and dosage settings. Such a touch pad can be designed for blind users in order to enable blind users to use such an application assembly, too.

The energy storage can be exchangeably arranged so that the functionality is ensured at any time. Alternatively, the assembly may be provided with a wireless chargeable and/or exchangeable energy storage. It may then easily remain with the patient at all times. The energy storage can be wirelessly charged by electromagnetic induction like an electrical toothbrush.

The assembly can be used in a network for the transmission, saving and processing of data relating to the dosage of a medicament. The network may be provided with an application assembly with a transmitter for the transmission of data relating to the selected and/or administered dosage of a medicament, a receiver for receiving the signal and a data processing unit for saving and processing the received data.

Personalized data may be saved in the data processing unit and means may be provided for processing the data transmitted by the transmitter together with the personalized data.

The network may comprise a base station which collects data of the application assembly and transmits them to the data processing unit. The signals of the application assembly may be wireless transmitted. The transmission between the base station and the data processing unit may be effected via a mobile telephone network.

Further modifications of the invention are subject matter of the subclaims. Preferred embodiments are described below in greater detail with reference to the accompanying drawings.

BRIEF DESCRIPTION OF THE SEVERAL
VIEWS OF THE DRAWINGS

Figure 1:
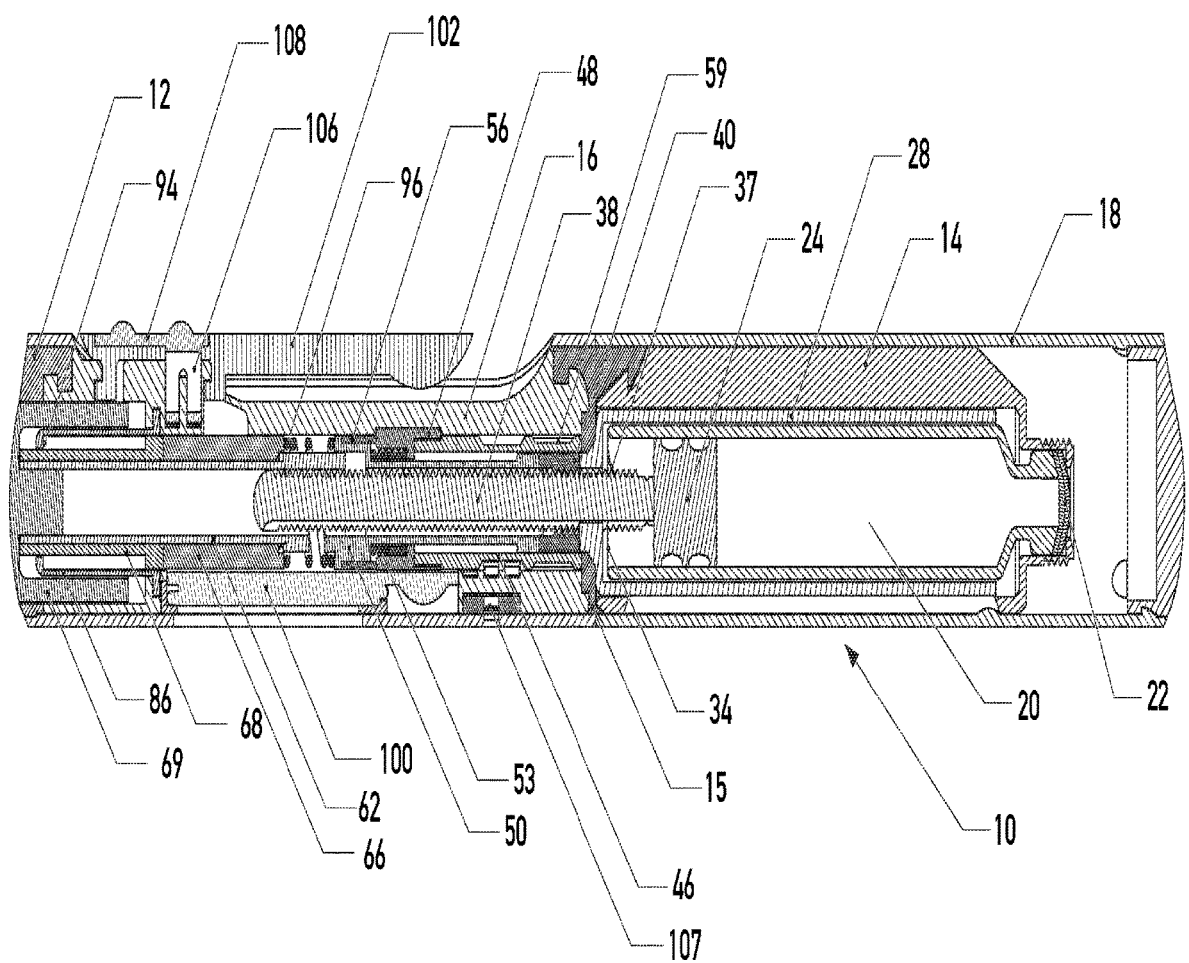
FIG. 1 is a cross section through an application assembly for insulin with mechanical setting of the dosage.
Figure 4:
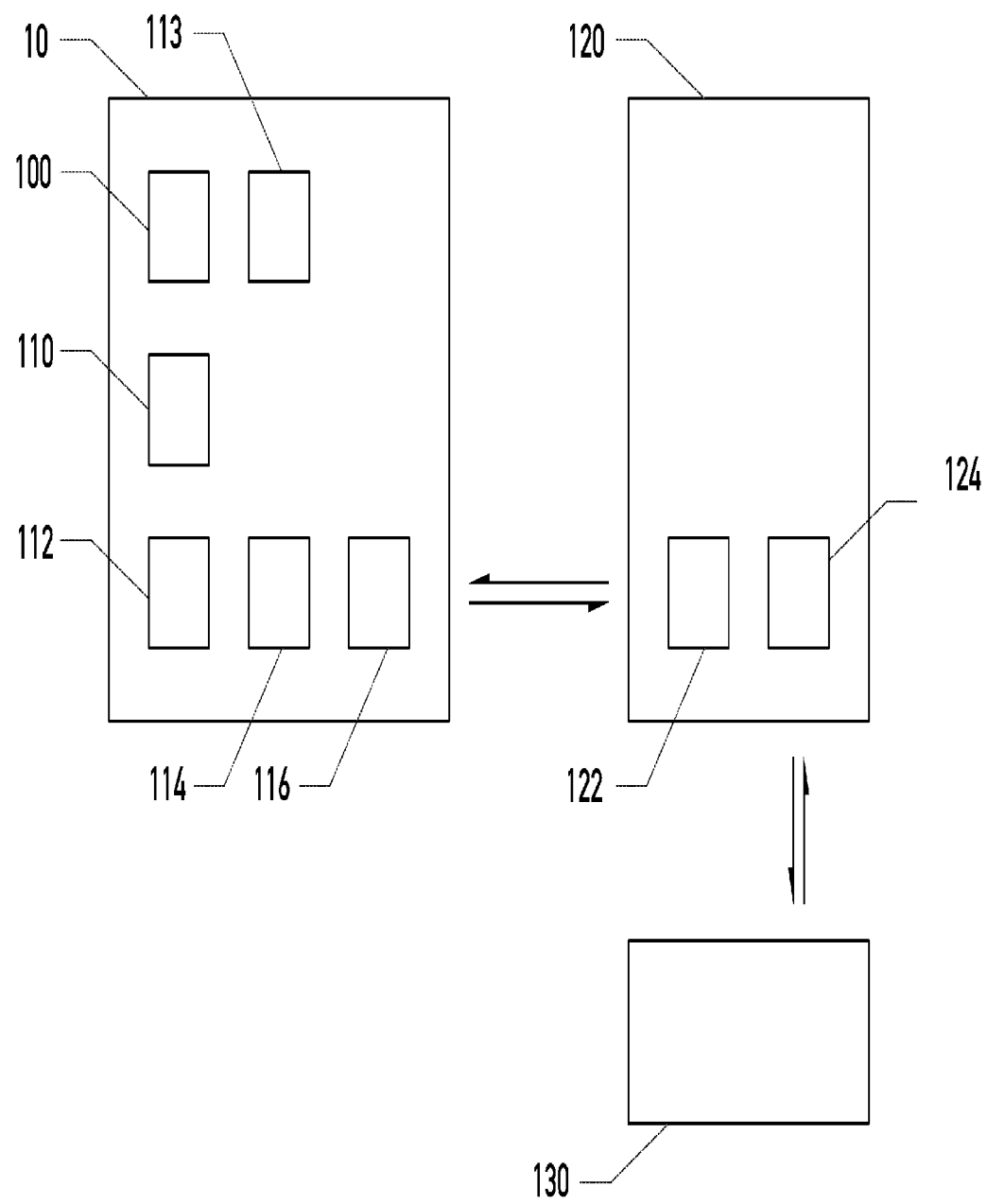
Figure 5:
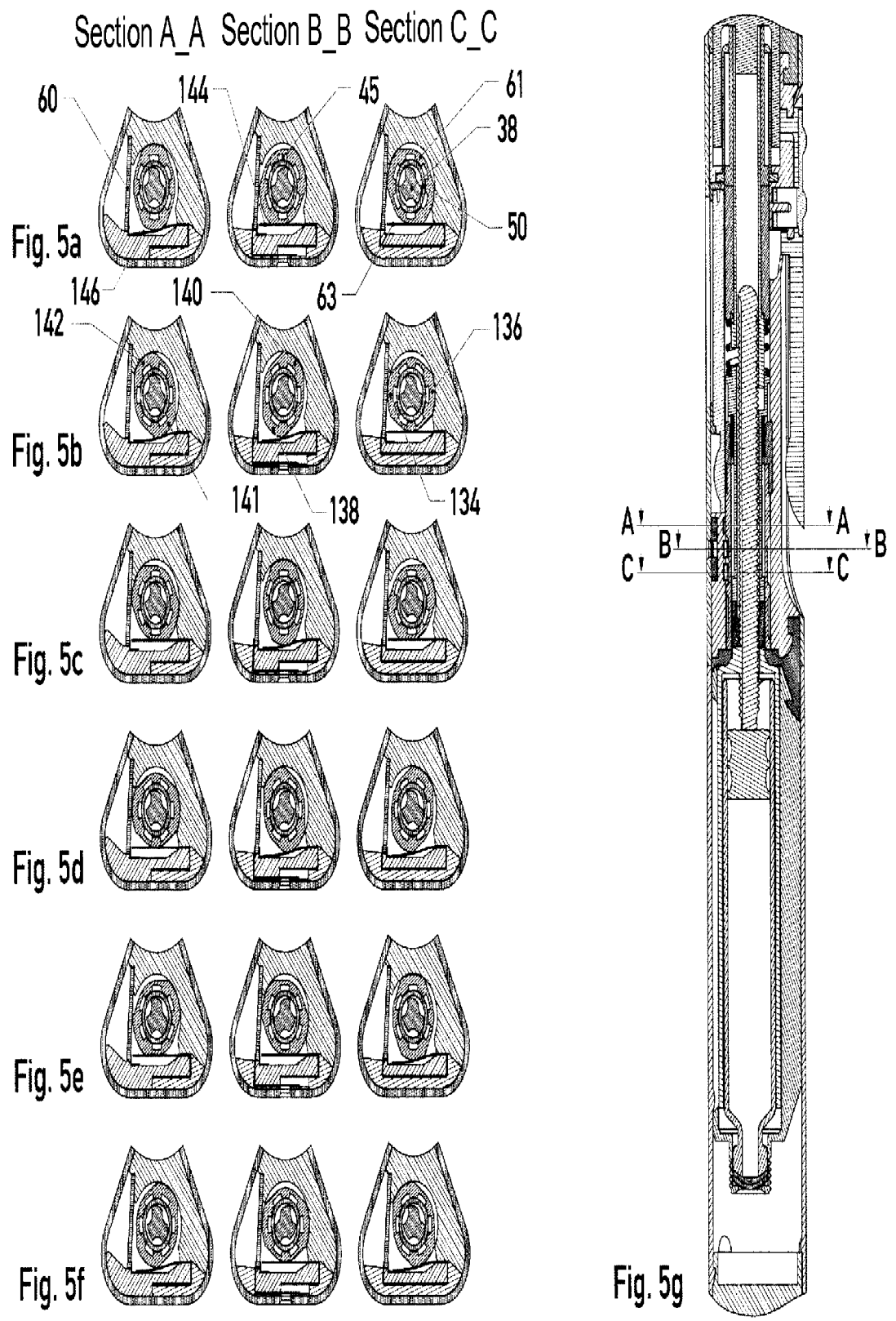
Figure 6:
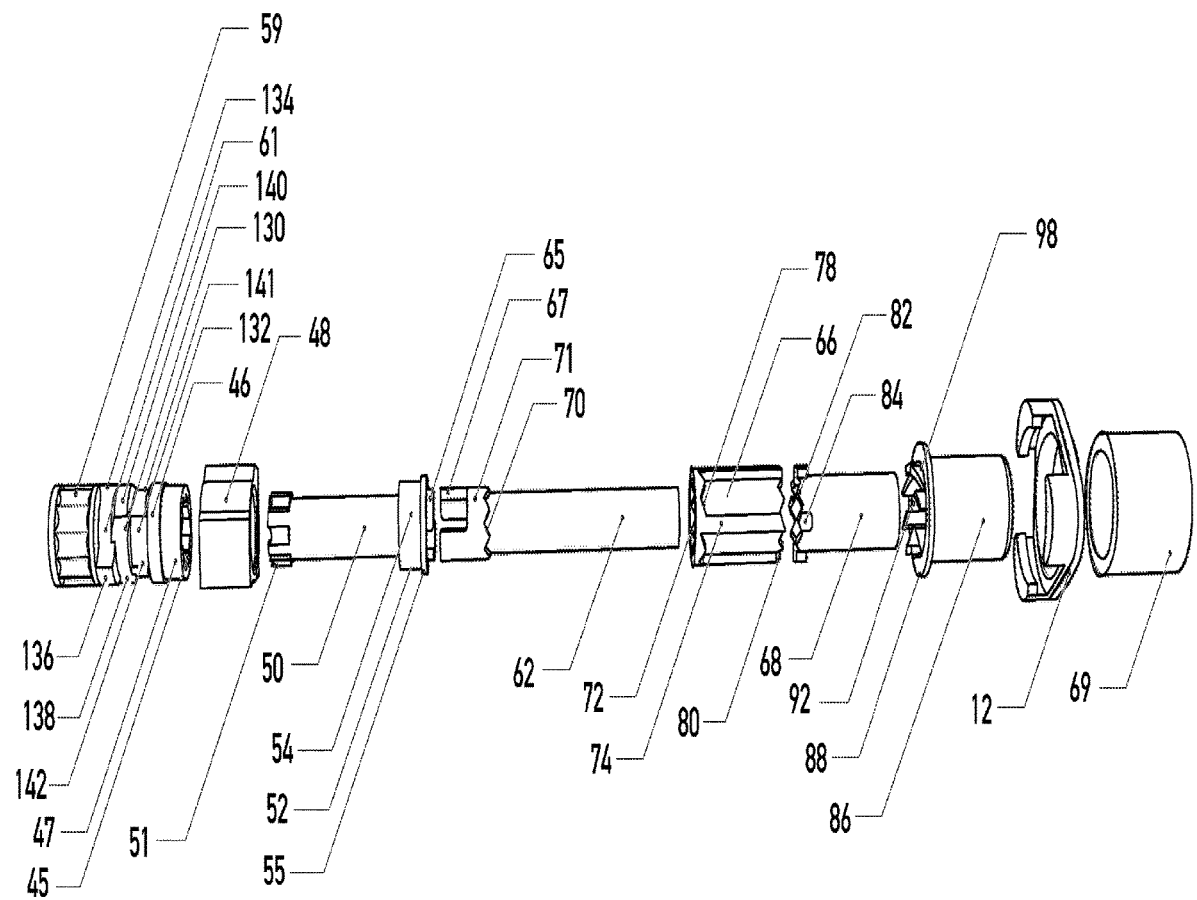
Figure 7:
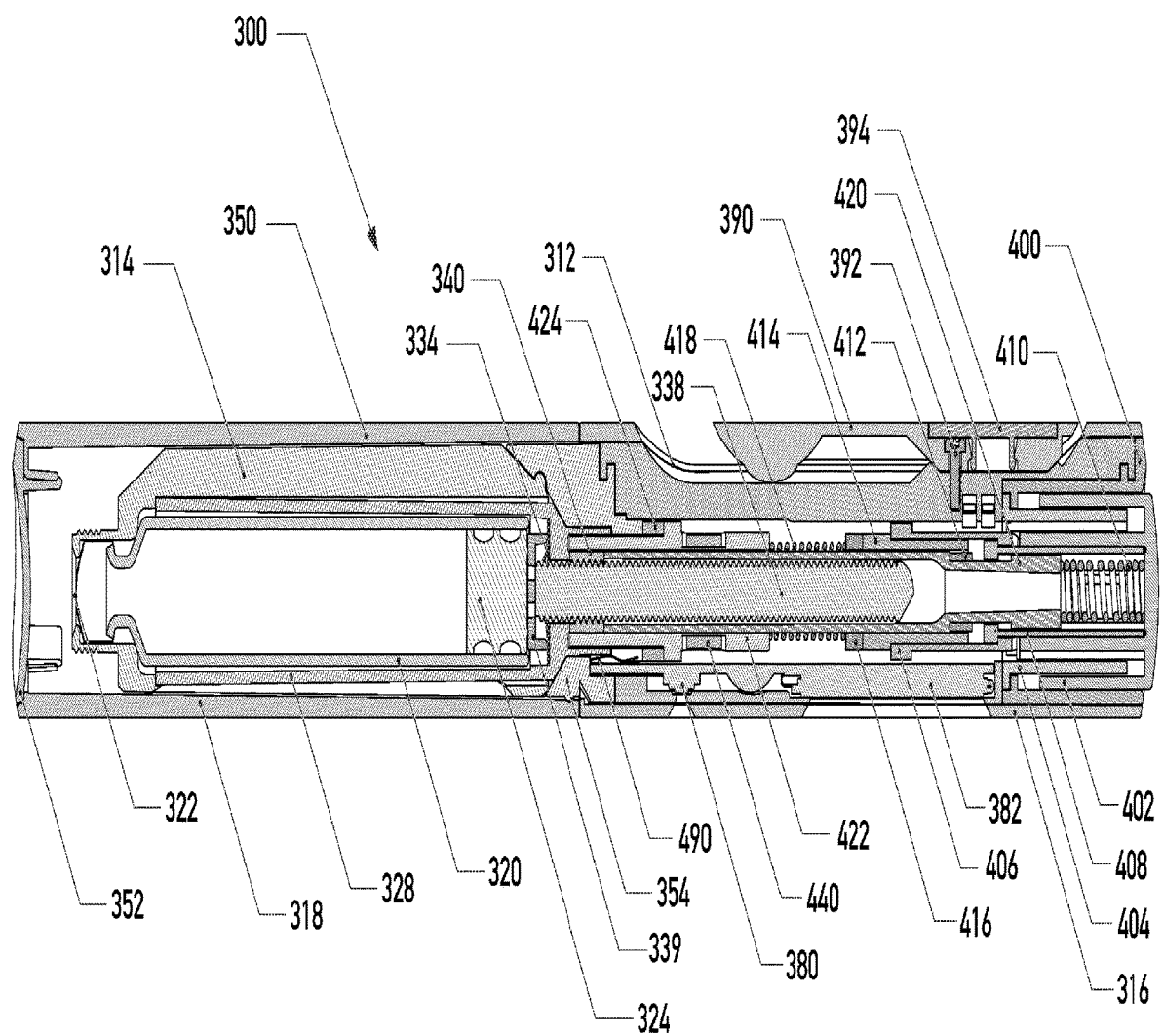
Figure 8:
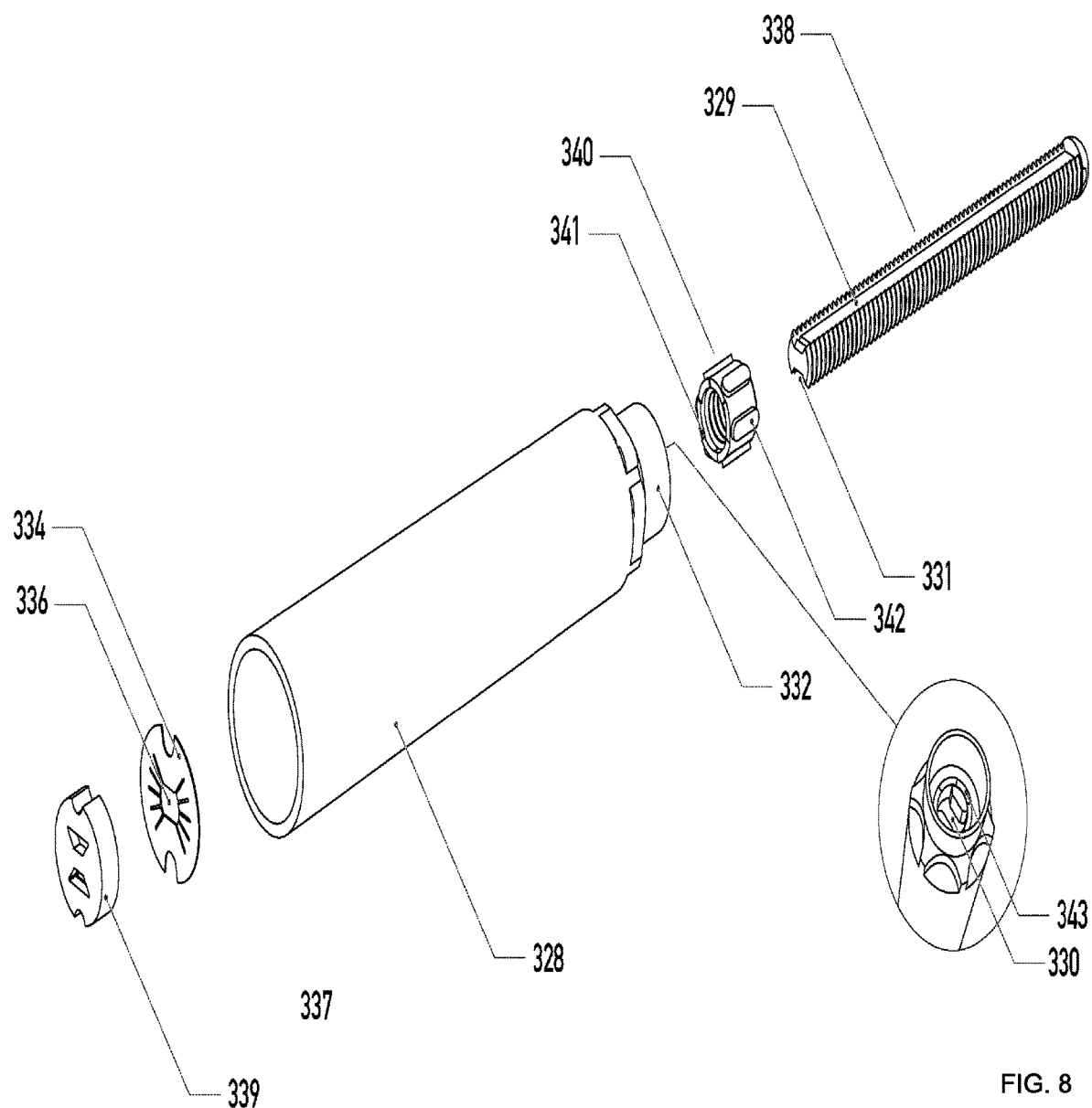
Figure 10:
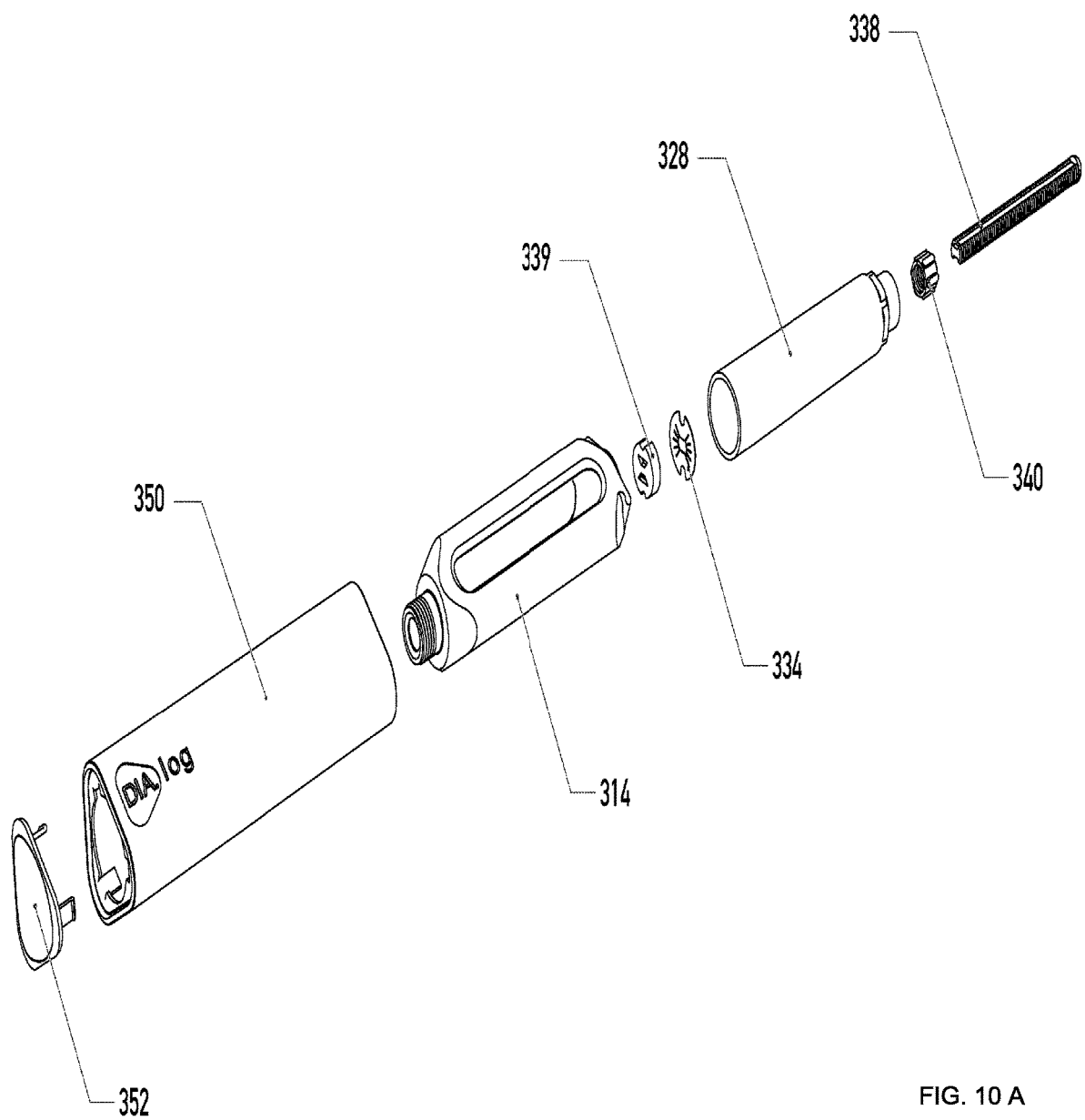
Figure 10B:
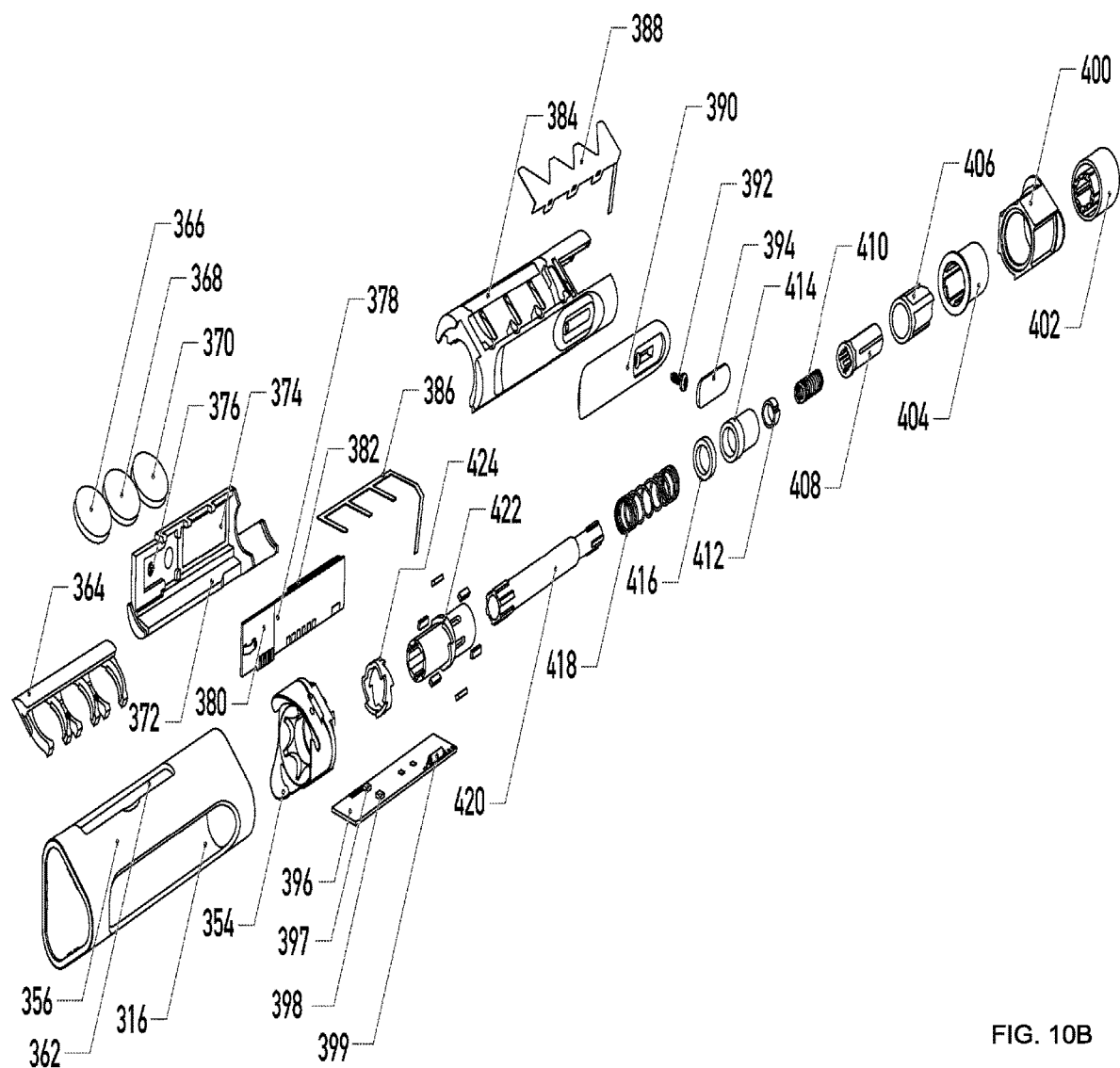
Figure 11A:
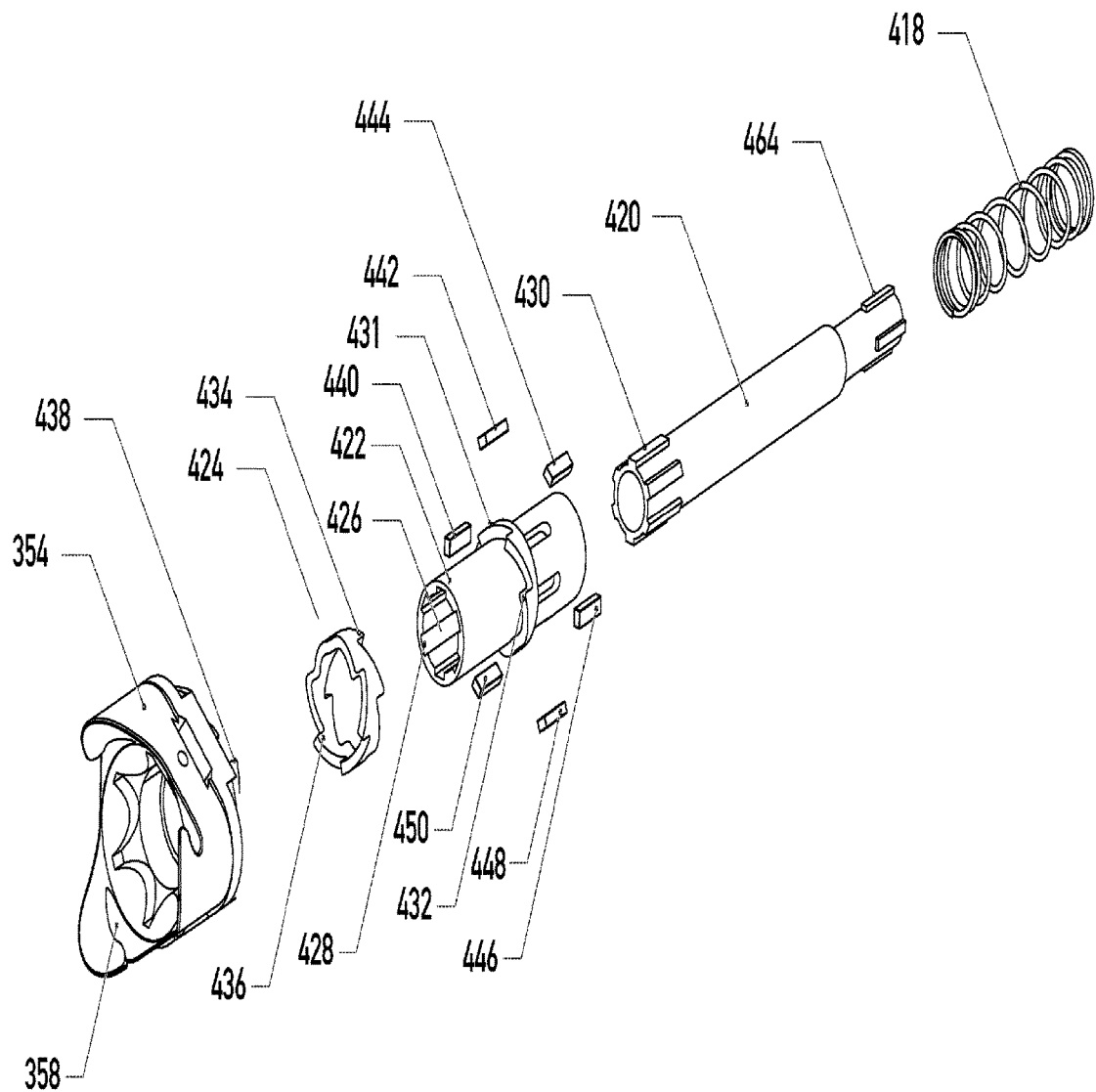
Figure 11B:
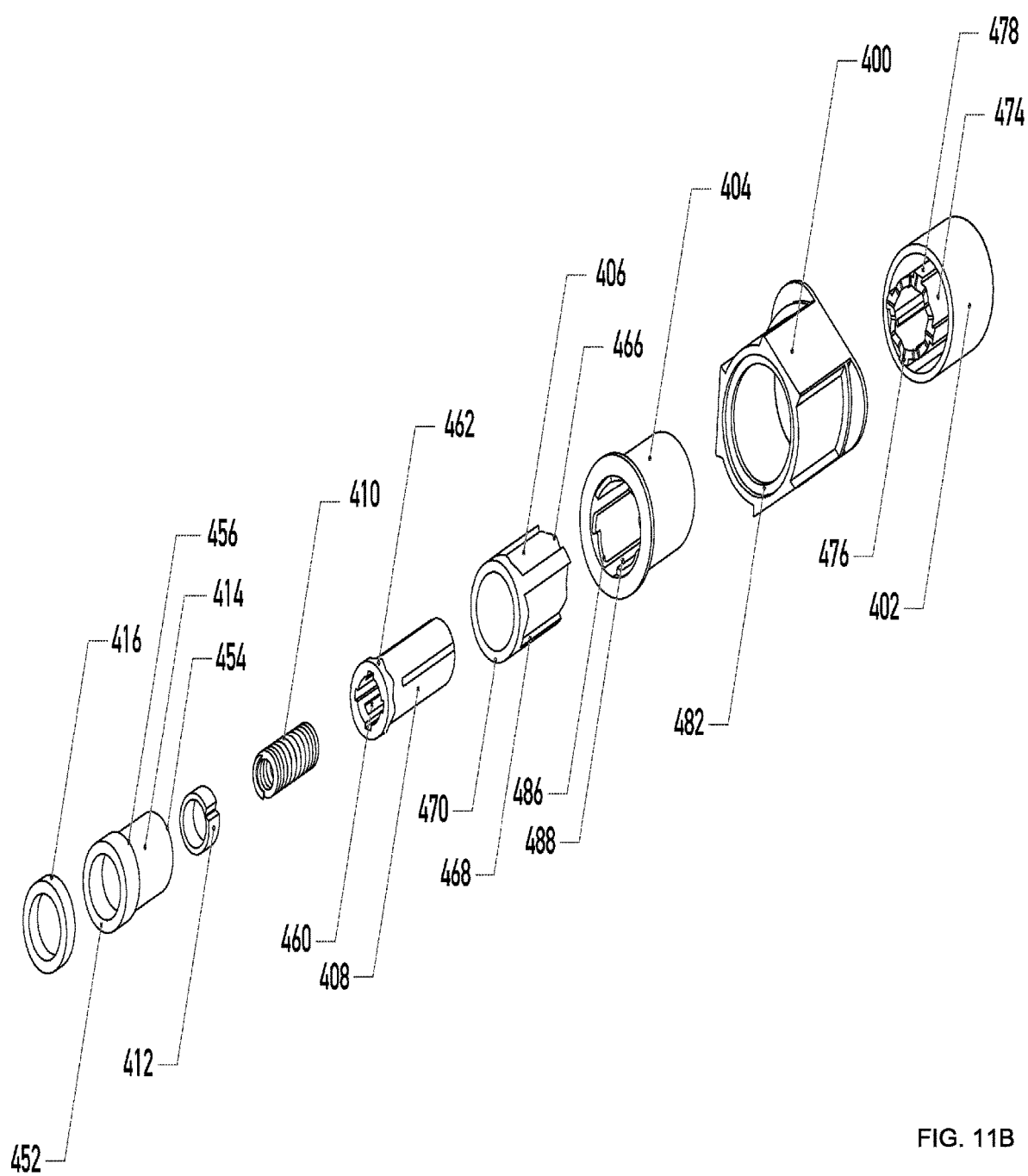

FIG. 4 schematically shows the setup of a network for an application assembly according to FIG. 1 with a data processing unit where patient data are stored;

FIGS. 5(a-f) shows cross sections along three different sectional planes of the assembly in FIG. 1 with different orientations of the dosage means;

FIG. 5g shows a cross section through an application assembly as in FIG. 1 with the three different sectional planes of FIGS. 5(a-f) shown;

FIG. 6 is an exploded view of the mechanical set-up of the application assembly of FIG. 1 which controls the movement of the dose setting knob along the longitudinal axis of the assembly;

FIG. 7 is a longitudinal cross section of an alternative embodiment of an application assembly where the dosage is contactless measured;

FIG. 8 shows an adapter of FIG. 7 in detail with a cartridge to adapt to an application assembly for insulin;

FIGS. 9(a-c) illustrates the locking mechanism during the dosing of insulin with an assembly of FIG. 7;

FIG. 10a is an exploded view of the cartridge side portion of the assembly of FIG. 7;

FIG. 10b is an exploded view of the dose setting knob side portion of the assembly of FIG. 7;

FIG. 11a is an exploded view of a portion of the mechanical set-up of FIG. 10b in greater detail;

FIG. 11b is an exploded view of another part of the mechanical set-up and the dose setting knob of FIG. 10b; and FIGS. 12(a-d) are cross sections perpendicular to the longitudinal axis of an application assembly of FIG. 7 in different positions.

DETAILED DESCRIPTION OF THE
INVENTION

In FIG. 1 an application assembly for insulin is generally denoted with numeral 10. The application assembly is provided with an elongated plastic housing. The housing comprises a front portion 14, a back portion 16, an intermediate portion 15 arranged between the front and the back portions 14 and 16, respectively, of the housing and an end portion 12. The front portion 14 of the housing is covered by an elongated cap 18.

An essentially cylindrical cartridge 20 is arranged inside the front portion 14 of the housing. The cartridge 20 is filled with insulin. The cartridge 20 is provided with a membrane 22. For administering the insulin a needle (not shown) can be inserted through the membrane 22.

The cartridge 20 is also provided with a plug 24 movably guided in an axial direction. The diameter of cartridges generally varies depending on the manufacturer. An adapter assembly is used to account for such variations. The adapter assembly has an exchangeable casing 28, a threaded rod 38, a nut 40 and a disk 34 and is described below in greater detail. Different adapter assemblies are used for different corresponding cartridges 20. The cartridge 20 is tightly supported in the adapter assembly. A dose setting knob 69 described below is present at the back portion 16 of the housing.

The adapter assembly comprises a casing 28. The cartridge 20 is arranged inside such casing 28. The casing 28 is essentially designed as a hollow cylinder. The inner diameter of the casing 28 corresponds to the outer diameter of the cartridge 20. The outer diameter of the casing 28 corresponds to the diameter of a cylindrical interior space of the front portion 14 of the housing. The casing 28 serves as an adapter for different cartridge shapes.

Figure 2:
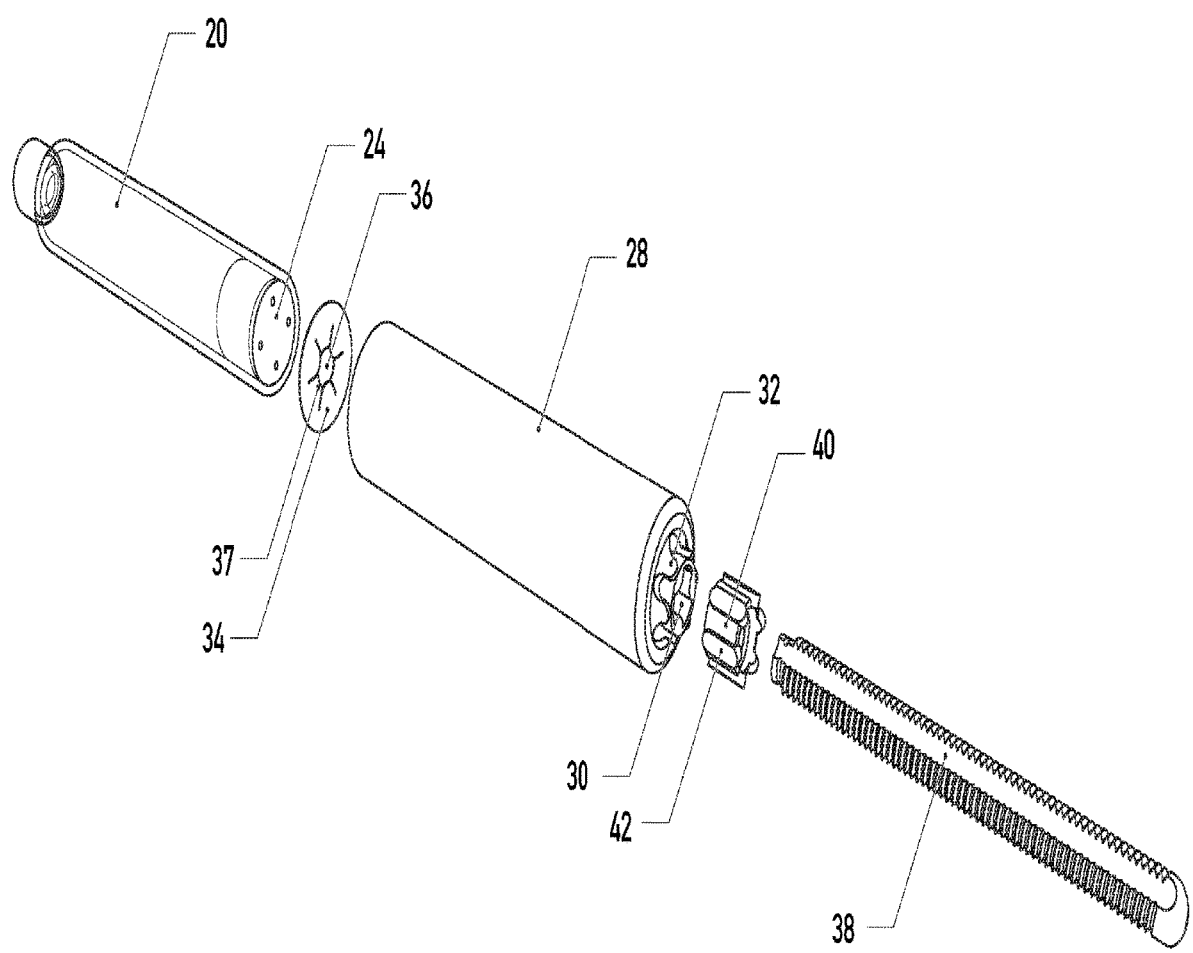
FIG. 2 shows an adapter with a cartridge to adapt the cartridge to the application assembly of FIG. 1 in greater detail.

The components 28, 38, 34, 40 of the adapter assembly are shown with a cartridge 20 in FIG. 2 in greater detail. The casing 28 is open at the cap end in order to enable the cartridge to be inserted when the front portion 14 of the housing is opened. The end of the casing 28 on the side of the dose setting knob 69 is closed and is provided with a central aperture 30. The aperture 30 is a circular opening with three inwardly rising radial projections. On the side of the dose setting knob 69 the front end of the cartridge 28 is provided with axial projections 32 form-fittingly engaging with depressions in the intermediate portion 15. Thereby, the casing 28 is secured against rotation.

The disk 34 essentially consists of sheet metal and is arranged adjacent to the closed end of the casing 28 on the side of the dose setting knob 69. The disk 34 is clamped between the cartridge 20 and the closed end of the casing 28. This is shown in FIG. 2. In FIG. 2 the disk is separately shown outside the casing 28 for better illustration. The disk 34 is also provided with a central opening 36. The opening 36 is star shaped. Thereby, small, concentric elastic sheet metal tongues 37 are formed. The number of elastic sheet metal tongues 37 depends on the symmetry of the star shaped opening 36. In the present case the disk 34 has six sheet metal tongues 37. Obviously, any other number of tongues is also suitable. The threaded rod 38 may be moved in an axial direction from the top in FIG. 1 through the aperture 30 and the opening 36 in the disk 34.

The threaded rod 38 is shape such that it corresponds to the form of the aperture 30. Thereby, the threaded rod 38 is secured against rotation with respect to the casing.

The threaded rod 38 is provided with a male, exterior thread. The elastic sheet metal tongues 37 engage with the threads of the threaded rod 38. Upon axial movement of the threaded rod 38 in the direction of the cartridge 20 the metal sheet tongues 7 are slightly bent. A movement of the threaded rod 38 in the reverse direction is prevented by the metal sheet tongues 37. The threaded rod 38 can only be axially moved in the direction of the cartridge. Insulin is pushed through the injection needle like a syringe upon axial, in FIG. 2 downward movement of the threaded rod 38 and the plug 24.

A nut 40 with a female thread is screwed onto the threaded rod 38 outside the casing 28. On its outside the nut 40 is provided with radial cams 42 for guiding the nut. Before putting a full cartridge into use the nut 40 touches the end of the casing 28 at the side of the dose setting knob. This is shown in FIG. 1. Upon rotation the nut 40 moves up in FIG. 1 relative to the casing. Thereby, a gap occurs between the nut 40 and the casing 28 which is fixed to the housing. Thereby, the plug 24 is not yet influenced. In order to administer insulin a pressure is applied to the threaded rod 38 and hence to the plug 24. In doing so, the threaded rod 38 is pushed downwards in FIG. 1 in the direction of the cap 18.

The upper end (FIG. 1) of the casing 28 forms a stop for the movement of the threaded rod 38 with the nut 40. The gap generated by rotating the nut 40 corresponds to the stroke travelled by the plug and is a measure for the administered dosage of insulin.

The slope of the thread of the threaded rod 38 is adapted to the geometry of the cartridge 20 and the applied insulin. A cartridge with a smaller diameter requires a greater slope than a cartridge with larger diameter for the same insulin and the same volume. One turn of the threaded rod 38 corresponds to a certain stroke and hence an administered dosage of insulin.

The dosing by rotating the nut 40 is carried out by means of a dosing means described below. The dosing means is arranged in the back portion 16 of the housing. This can be seen in FIGS. 1 and 6. The adapter assembly and the dosing means serve to select the dosage.

The dosing means comprises a jacket 46 with a cylindrical socket 47. With the cylindrical socket 47 the jacket 46 is pivotably mounted in a bearing sleeve 48. The inner wall of the jacket 46 is provided with axial grooves 45. The cams 42 of the nut engage with the grooves 45 and are axially movable therein.

A rotational movement of the jacket 46 is hence transferred to the nut 40. The nut 40 moves in an axial direction on the non-rotatable threaded rod 38. An axially movable, hollow shaft 50 is coaxially provided inside the jacket 46. At its end hidden inside the jacket 46 the hollow shaft 50 is provided with projections 51 extending in an axial direction along the circumference also engaging with the grooves 45 in the inner wall of the jacket 46. The jacket 46 hence follows a rotation of the hollow shaft 50.

The hollow shaft 50 is provided with a thickened portion 52 along the circumference at its dose setting knob end. The thickened portion 52 extends over a cylindrical range 54 ending at a surrounding edge 55 with a larger diameter. The thickened portion 52 serves as a counter bearing for a pressure spring 53 coaxially arranged around the hollow shaft 50. The pressure spring 53 is shown in FIG. 1. The counter bearing of the pressure spring 53 on the side of the cartridge is formed by the bearing sleeve 48.

The pressure spring 53 pushes the hollow shaft 50 from the jacket 46. The stroke is limited by a release spring 96 stopping the surrounding edge on the side of the dose setting knob. The release spring 96 is shown in FIG. 1. There is a gap between the nut 40 and the hollow shaft 50.

If the patient rotates the hollow shaft 50 the nut 40 is shifted in the jacket 46 in the direction of the dose setting knob 69. Thereby, the gap between the hollow shaft 50 and the nut 40 is reduced. At the same time the gap between the upper end, in FIG. 1, of the casing 28 and the nut 40 is increased. By exertion of a force onto the hollow shaft 50 downwards in FIG. 1 the compression spring 53 is compressed. The gap between the hollow shaft 50 and the nut 40 is reduced. Once the hollow shaft 50 touches the nut 40, the nut 40 moves in the direction of the cap 18 upon further application of a force onto the hollow shaft 50. As the nut is connected to the threaded rod 38 by the thread the threaded rod is shifted in the direction of the cap 18 until the nut meets the dose setting knob end of the casing 28.

The range 54 is surrounded by a conducting tube 56. The conducting tube 56 is shown in FIG. 1. Metal contacts are attached to bearing sleeve 48 on the side of the dose setting knob. A switch is formed by interaction with the conducting tube 56.

Closing the switch indicates that insulin is administered. The opening of the switch is used as a switch-on post. In a different embodiment (not shown) a magnetically induced sensor mechanism is provided which realizes the switching operations by moving a magnet fixed to the bearing sleeve 48 relative to a magnetic sensor attached to a printed circuit board.

On its outside the jacket 46 is divided into three portions. A first portion is provided with several radial projections 59 on the circumference. Movable latching elements 33a and 33b (shown in FIG. 3) provided in the back portion 16 of the housing engage with the projections 59. Thereby, the rotational movement of the jacket 46 is divided into angular steps. The division is chosen in such a way that every latching in the next position corresponds to a rotation of the hollow shaft 50 by 30°.

Figure 3:
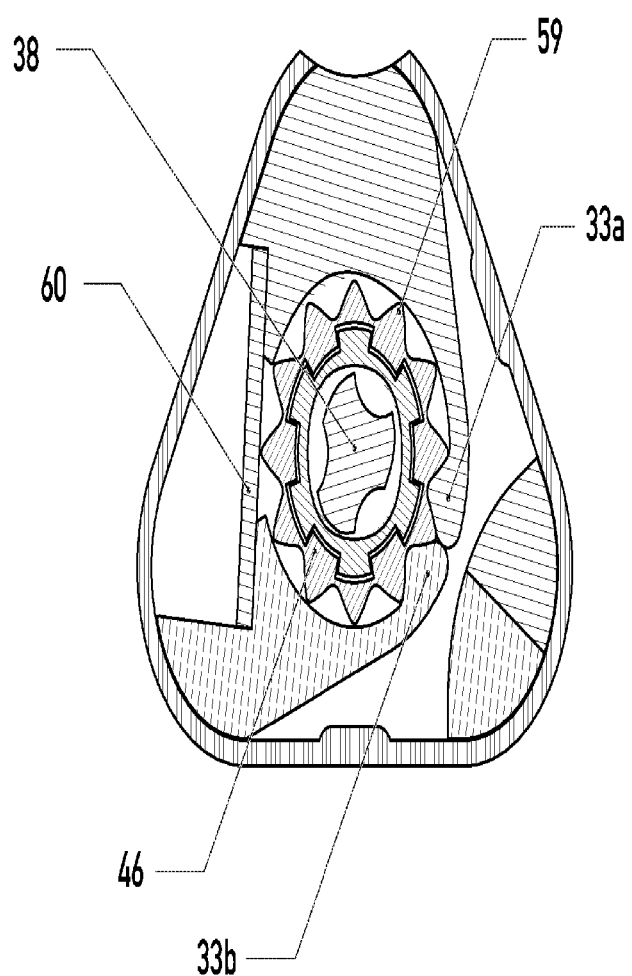
FIG. 3 is a cross section of the application assembly of FIG. 1 perpendicular to its longitudinal axis.

A second portion of the jacket 46 is provided with three axial cam discs 61, 130 and 132. Each cam disc 61 comprises two diametrically opposite cams 134, 136, 138, 140, 141 and 142. The cam discs 61 are angularly displaced by 60° with respect to each other. A spring contact 63, 144 and 146 is provided in the back portion 16 of the housing on the same axial level as each cam disk 61, 130 and 132. This is shown in FIG. 5. The spring contacts 63, 144 and 146 are attached to a circuit board 60. The circuit board 60 is positioned in the back portion 16 of the housing (FIG. 3).

Upon rotation of the jacket 46 the spring contacts 63, 144 and 146 are alternately moved by the cams 134, 136, 138, 140, 141 and 142. Thereby, the contacts are opened or closed. FIG. 5 shows the cams 134, 136, 138, 140, 141 and 142 and the position of the spring contacts 63, 144, 146 for a counter-clockwise rotation. A counter-clockwise rotation results in positions shown in the spreadsheet below. A closed contact is represent by 1 an open contact by 0.

| FIG. | pivot angle | cam disk A | cam disk B | cam disk C |
|---|---|---|---|---|
| 5a | 0° | 1 | 0 | 0 |
| 5b | 30° | 1 | 1 | 0 |
| 5c | 60° | 0 | 1 | 0 |
| 5d | 90° | 0 | 1 | 1 |
| 5e | 120° | 0 | 0 | 1 |
| 5f | 180° | 1 | 0 | 1 |

Starting from a position with a pivot angle of 0° a counter-clockwise rotation leads to the following encoding for the first 30° rotation:

| pivot angle | cam disk A | cam disk B | cam disk C |
|---|---|---|---|
| 0° | 1 | 0 | 0 |
| −30° | 1 | 0 | 1 |

The rotating direction of the jacket 46 can be unambiguously assigned by the order in which the contacts open (0) and close (1). A corresponding insulin dosage is related to the sequence of the switch positions. The third contact essentially serves for reliability and can be used to detect errors.

The hollow shaft 50 is provided with a first claw 65 on the side of the dose setting knob. This is shown in FIG. 6. A second claw 67 of an extension 62 engages with the first claw 65 of the hollow shaft 50. The extension 62 is also hollow. The second claw 67 is provided on the cap side of the extension 62. The dose setting knob 69 is attached on the other side of the extension. When the patient rotates the dose setting knob, the extension 62 follows the rotational movement. The extension 62 transmits the rotation through claw 67 to claw 65. A rotation of the dose setting knob is hence transmitted to the hollow shaft 50 and through the hollow shaft to the nut 40.

The claws 65 and 67 allow an axial movement of hollow shaft 50 and extension 62 with respect to each other due to the presence of a gap. A shoulder 71 is provided at the second claw 67 on the side of the dose setting knob. The extension 62 is conical beyond the shoulder. On the side of the dose setting knob the shoulder 71 is provided with a spur gearing 70.

An infeed jacket 66 is shifted over the extension 62. The infeed jacket 66 has two sides: on the side of the cap 18 and one on the side of the dose setting knob 69. A spur gearing 72 is provided on the side of the cap 18 the spur gearing engaging with the spur gearing 70 of the shoulder 71.

Four angularly symmetrical guiding rails 74 are provided along the outside of the infeed jacket 66. A ring 76 on the side of the cap connects the guiding rails 74 with the infeed jacket 66. The ring 76 is provided with a tooth shaped wave track 78 on the opposite side. The tooth shaped wave track 78 is interrupted by the guiding rails 74. On the side of the dose setting knob 69 the end of the guiding rails 74 is provided with a saw tooth shape.

The dose setting knob end of the infeed jacket 66 is provided with a first tooth shaped structure 80 cooperating with a second tooth shaped structure 82 of a push jacket 68. The push jacket 68 is also coaxially arranged on the extension 62. At its cap end the push jacket 68 is provided with projections 84 on the outside.

A guiding bushing 86 is rotatably beared in the back portion 16 of the housing. Therefore, the guiding bushing 86 is provided with a brim 88 on its outside. Corresponding to the brim 88 a radial groove 90 is provided in the back portion 16 of the housing. The brim and the radial grove 90 form a bush bearing. In an alternative embodiment which is not shown the guiding bushing 86 is not rotatable.

The guiding bushing 86 is provided with guiding grooves 92. The numbers of guiding grooves 92 correspond to the numbers of projections 84 of the push jacket 68 and the numbers of guiding rails 74 of the infeed jacket 66. The push jacket 68 is axially movable in the guiding bushing 86. A dose setting knob end of the guiding bushing is provided with a block 94 for the infeed jacket 66. The block 94 is shown in FIG. 1.

The cap end of the guiding bushing 86 is provided with a saw tooth shaped spur gearing 98 that correspond with the saw tooth shaped ends of the infeed jacket 66. The saw teeth 98 of the guiding bushing 86 are formed in such a way that a guiding groove 92 is arranged after every second steep flank.

The above mentioned release spring 96 is arranged axially between the hollow shaft 50 and the infeed jacket 66. The release spring 96 is shown in FIG. 1. The release spring pushes both claws 65 and 67 apart.

The spring constant of the release spring 96 is larger than the spring constant of the pressure spring 53. Hence, in first approximation the pressure spring 53 is compressed first before the release spring 96.

The release spring 96 and the pressure spring 53 load the infeed jacket 66 with a force acting in the direction of the dose setting knob 69. Thereby, the infeed jacket 66 is pushed against the guiding bushing 86.

If the infeed jacket 66 engages with its guiding rails 74 in the guiding grooves 92 the infeed jacket 66 moves by the spring force of the pressure spring 53 in the direction of the end portion 12. Together with the infeed jacket 66 the push jacket 68 moves in the guiding bushing 86 until the projections 84 of the push jacket 68 reach the block 94 of the guiding grooves 92 in the guiding bushing 86. This defines the first position of the infeed jacket 66. The dose setting knob 69 is now accessible and can be rotated and otherwise operated.

By pushing the dose setting knob 69 at first the pressure spring 53 is compressed. The push jacket 68 moves in the direction of the cap 18. Thereby, the infeed jacket 66, the extension 62 and the hollow shaft 50 are also moved in that direction. When the conducting tube 56 reaches the metal contacts at the bearing sleeve 48, the switch is closed.

Thereby, the administered insulin dosage is saved. Additionally, a time stamp is generated and saved in a memory. The insulin pen is in an energy saving mode.

The release spring 96 is compressed by further pressure on the dose setting knob 69. Thereby, the distance between the claws 65 and 67 is reduced. When the guiding rails 74 of the infeed jacket 66 are not guided by the guiding grooves 92 of the guiding bushing 86 the infeed jacket 66 is turned further one saw tooth of the guiding bushing 86 by the spur gearing between push jacket 68 and infeed jacket 66.

There are no guiding grooves corresponding to the guiding rails 74 of the infeed jacket 66. If the dose setting knob 69 is not pushed anymore the release spring relaxes and pushes the infeed jacket 66 against the guiding bushing 86. The infeed jacket 66 is locked in that position.

In this position the dose setting knob 69 is hidden in the housing of the assembly. The dose setting knob 69 is secured against accidental actuation.

With repeated pushing of the dose setting knob 69 in the direction of the cap 18 the release spring is compressed. The push jacket 68 pushes the infeed jacket 66 in the direction of the cap 18. When the guiding rails 74 of the infeed jacket 66 are shoved over the steep edge of the saw tooth shaped spur gear 98 of the guiding bushing 86 by effect of the spur gear between push jacket 68 and infeed jacket 66 the infeed jacket 66 is rotated further one saw tooth of the guiding bushing 86.

The guiding rails of the infeed jacket 66 now accompany corresponding guiding grooves 74 of the guiding bushing 86. Upon releasing the dose setting knob 69 the infeed jacket 66 moves in the direction of the end portion 12. Thereby, the dose setting knob 69 moves out of the end portion 12. The dose setting knob is now accessible and can be rotated and can be otherwise operated.

A display 100 is provided at the assembly 10. The casing is also provided with a clip 102. This serves for the attachment of the assembly to a pocket or the like. Furthermore, a color coding is provided at the back portion 16 of the housing. This allows for a color coding of different insulin.

A switch 106 activates the assembly 10 upon first initiation. It is understood that the first activation can also be conducted by inserting batteries. The batteries are exchangeable.

The application assembly 10 is switched on and off by operating the dose setting knob 69. If the application assembly is switched on the last applied insulin dosage and the point in time of the last application are displayed on the display 100. A timer 110 shown in FIG. 4 determines the time. A processor 112 then calculates the time of the day and the date. At predefined times the contents of the memory 114 are sent by a radio circuit. The transmitted signal can also be manually triggered. A switch 107 is provided for this purpose.

In FIG. 4*a* schematic of a network is shown. The network comprises an application assembly 10, a base station 120 and a data processing unit 130.

The application assembly comprises the memory 114, a sending and receiving arrangement 116 and a timer 110. The application assembly 10 can communicate with the base station 120. Therefore, a sending and receiving arrangement 122 is provided in the base station.

The communication is bi-directionally established by radio frequencies, for example in the frequency range of 868 MHz. Upon insertion of the batteries the application assembly 10 searches for the base station 120. Radio signals are emitted for this purpose.

The base station 120 receives this signal and sends a signal to the application assembly 10. Then, the timer 110 inside the application assembly 10 is started. The base station 120 also transmits the next communication time to the application assembly 10. The application assembly then sends a signal to the base station 120 at predefined times.

If the application assembly does not receive a signal from the base station within a certain time interval the application assembly stops broadcasting. Thereby, the battery of the application assembly 10 is not unnecessarily used up.

If communication with the base station is established the application assembly 10 broadcasts the saved, applied insulin dosages with the corresponding timestamp. The base station 120 transmits the data received from the application assembly 10 to a data processing unit 130.

This transmission is carried out by a modem 124 provided in the base station 120. In the present embodiment the modem uses the mobile network standard GSM. The base station 120 logs in the data processing unit via modem 124. Subsequently, data are exchanged. The data in the data processing unit are accessible by a web interface. The web interface allows for settings at the base station or at the application assembly.

An alternative embodiment of an application assembly generally denoted with numeral 300 is shown in FIG. 7.

As in the previous embodiment the application assembly 300 is provided with a casing 312 with a cap 318 and a cartridge 320, which is separated into a front portion of the casing 314 and a back portion of the casing 316. The cartridge 320 is provided with a membrane 322 and a plug 324. The cartridge 320 is held in an adapter assembly to adapt cartridges of different suppliers and dimensions to the present application assembly. A switch 490 detects whether an adapter assembly is inserted.

The adapter assembly of the present embodiment comprises, as in the previous embodiment, a casing 328, a threaded rod 338, a disk 334 and a disk 340, as well as an additional plunger 339. The components of the adapter assembly are separately shown in FIG. 8 in greater detail. The functionality of the adapter assembly does not essentially differ from the adapter assembly of the above described embodiment. The cap side of the plunger 339 is clipped to the threaded rod 338. Therefore, the pressure is evenly distributed on the plug 324.

The dose setting knob end of the casing 324 is closed and is provided with a central aperture 330. The aperture 330 is a circular opening with two inwardly rising radial projections. The profile of the threaded rod is provided with two corresponding depressions 329 and 331.

The disk 334 is provided with an oval opening 336 adapted to the cross section of the threaded rod. The edge of the opening 336 is partially provided with radial slits. Thereby, small concentric tongues 337 are formed of elastic sheet metal. The threaded rod 338 extends through the aperture 330.

The nut 340 follows the rotation of the dose setting knob 402 by a mechanical design described below. The cap side of the nut 340 is provided with a saw tooth shaped spur gear 341. The spur gear 341 of the nut 340 engages with a corresponding spur gear 343 at the casing 328. The slope of the saw teeth correspond to the slope of the thread of the threaded rod 338. Thereby, it is ensured that only predefined units can be administered.

Figure 9A:
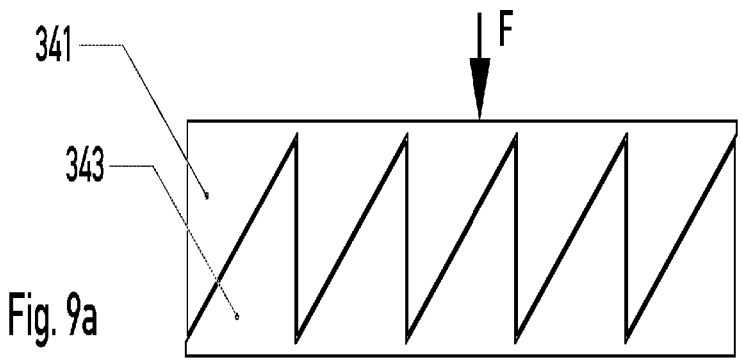
Figure 9B:
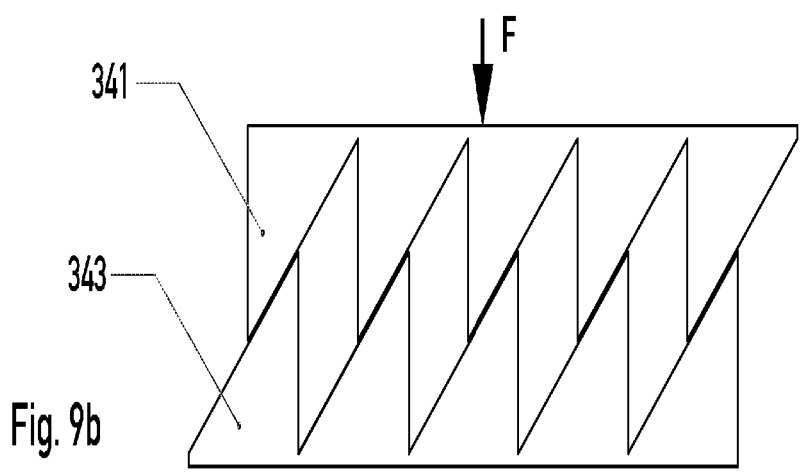
Figure 9C:
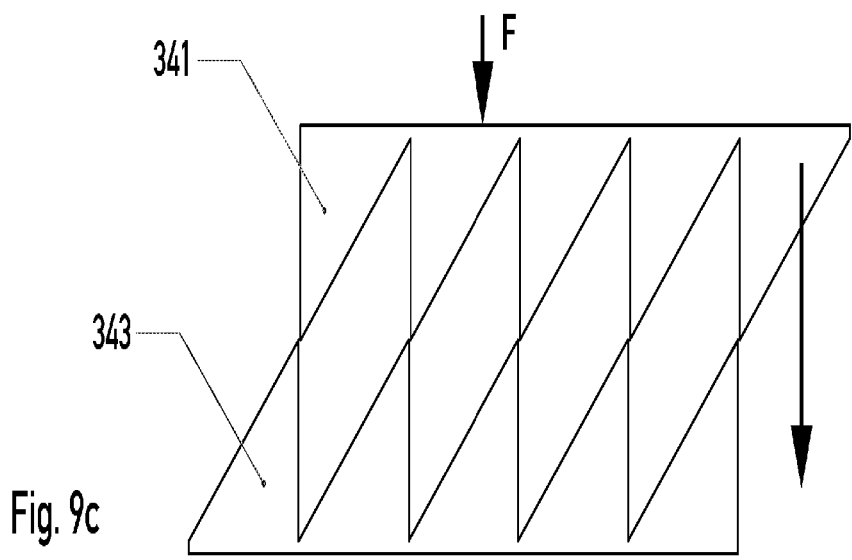

The functional principle of the dosing is illustrated in FIGS. 9(*a-c*). Before application both toothings are on top of each other. This is shown in FIG. 9*a*. If the nut 340 on the threaded rod is rotated the toothing 341 is shifted against the toothing 343. The inclined edges of the toothing are still in touch. A force F that acts in the marked direction does not lead to an axial movement of the threaded rod. This can be seen in FIG. 9*b*. When the nut is shifted so far that the steep flanks of the toothing face each other the threaded rod can be moved in the direction of the cap by the marked force F. This is shown in FIG. 9*c*. The mechanism improves the accuracy of applications.

The cap 318 is formed by a tube 350 with an essentially triangular cross section. This can be well seen in FIG. 10*a*. One end of the triangular tube 350 is closed by an end piece 352. The front portion of the casing 314 serves as reception for the casing 328 of the adapter assembly 327. The plunger 339 and the disk 334 are arranged in the casing 328. The nut 340 and the threaded rod 338 extend into the back portion of the casing 316. This can be seen in FIG. 7. The portion of the casing 316 comprises an elongated corpus 356 also having an essentially triangular cross section. This is shown in FIG. 10b. An intermediate piece 354 is located between the portion of the casing 314 and the corpus 356.

The intermediate piece 354 is provided with a bayonet coupling having the front portion of the casing 314 attached thereto. The intermediate piece 354 is provided with depressions 360 that engage with projections 332 in the casing 328. The casing 328 is hence secured against rotation.

A display and control panel 372 is fitted into the corpus 356. The display and control panel 372 comprises a display window 374 and an operator panel 376. A control sensor 380 which is addressed by the control panel 376 is located on a display circuit board 378. Furthermore, a display 382 is located on the display circuit board 378.

A slit 362 for a battery holder 364 is provided at the corpus 356. The battery holder 364 holds batteries or accumulators 366, 368 and 370 providing the application assembly 300 with electricity. The battery holder 364 holds the batteries 366, 368 and 370 in a battery compartment 384. The battery compartment 384 is also provided in corpus 356.

A contact strip 386 connects the plus terminal of the batteries 366, 368 and 370 with the display circuit board 378. The negative terminal of the batteries 366, 368 and 370 is connected to the display circuit board 378 via a sheet metal tongue 388.

A clip 390 is attached to the battery compartment 384 by a screw 392. A clip cover 394 covers the screw 392.

A sensor circuit board 396 is electrically connected to the display circuit board 378. Two magnetic sensors 397 and 398 are provided on the sensor circuit board 396. An ON-sensor 399 is also provided on the circuit board. A knob enclosure 400 forms one end of the corpus 356.

The actual mechanical design of the application assembly comprises, from the right to the left: the dose setting knob 402 the knob enclosure 400, a hat element 404, a crown 406, a counter crown, 408, a balance spring 410, a securing ring 412, a block 414, a ring magnet, 416, a pressure spring 418, a shaft 420, a coupling element 422 and a latch element 424. The interaction of the components is described below with reference to FIGS. 11a and 11b.

The coupling element 422 connects the nut 340 to the shaft 420. The coupling element 422 is rotationally symmetrical about a longitudinal axis of the application assembly 300. The coupling element 422 is pivotably mounted in a space formed by the display—and control panel 372 and the battery compartment 384.

The coupling element 422 is provided with a longitudinal bore hole 426. The inner wall of the coupling element 422 is provided with guiding grooves 428. The attachments 342 provided on the nut 340 are guided in the guiding grooves 428. The nut 340 is movable along the axis of the coupling element 422 and follows the rotation of the coupling element 422. As the nut 340 is located on the threaded rod 388 it 340 moves in the axial direction of the coupling element 422.

A shaft 420 is guided in the coupling element 422. Radial, outwardly projecting noses 430 are provided with at the end of the shaft hidden in the coupling element 422, the noses cooperating with the guiding grooves 428 of the coupling 422. The shaft 420 is movable in an axial direction along the guiding grooves 428. The coupling 422 is charged with the spring force of a pressure spring 418. On the side of the dose setting knob the shaft 420 has a reduced diameter for receiving a securing ring 412.

The coupling element is provided with a circumferentially thickened portion 431. On the cap side of the thickened portion 431 a saw tooth profile 432 is provided. The saw tooth profile 432 engages with a corresponding profile 343 of the latch element 424.

Upon, for example, clockwise rotation of the shaft 420 the saw teeth disabling and the coupling element 422 moves against the spring force of the pressure spring 418. As soon as the steep flanks of the saw teeth face each other the pressure spring 418 relaxes and shifts the coupling element 422 against the latch element 424.

This movement is audible as well as tangible. The latch element 424 and the coupling element 422 form an acoustic and haptic feedback for setting a selected dosage by rotation.

In order to provide a feedback upon rotation in the opposite direction, i.e. in this example counter-clockwise, the latch element is provided with another spur gear 436 on the opposite side. This is directed in the opposite direction and engages with a saw tooth profile 438 that is provided on the dose setting knob side of the intermediate portion 354. Upon rotation in a clockwise direction the teeth of the spur gear 436 and the saw tooth profile 438 jam. The coupling element 422 and the latch element rotate with respect to each other and provide the feedback. Upon a rotation in a counter-clockwise direction the effect reverts. Latch element 424 and coupling element 422 jam up and the latch element moves with respect to the intermediate piece 354 whereby the respective toothing provide the acoustic and haptic feedback.

Six bar magnets 440, 442, 444, 446, 448 and 450 are arranged along the circumference of the coupling element 422. The orientation is chosen in such a way that a north and a south pole are alternatively revolving. A magnetic field is formed between each neighboring pole running from north to south pole.

The orientation of the magnetic fields is detected and processed by to magnetic sensors 397 and 398 on the sensor circuit board 396. The principle is shown in FIGS. 12(a-d). FIG. 12 shows a cross section of the magnets. Magnetic sensors 397 and 398 are located on the sensor circuit board 396. The magnetic sensors 397 and 398 react on the penetration direction of a magnetic field penetrating the sensor surface. The signals generated by the magnetic sensors are discussed below on the basis of a clockwise rotation.

Figure 12A:
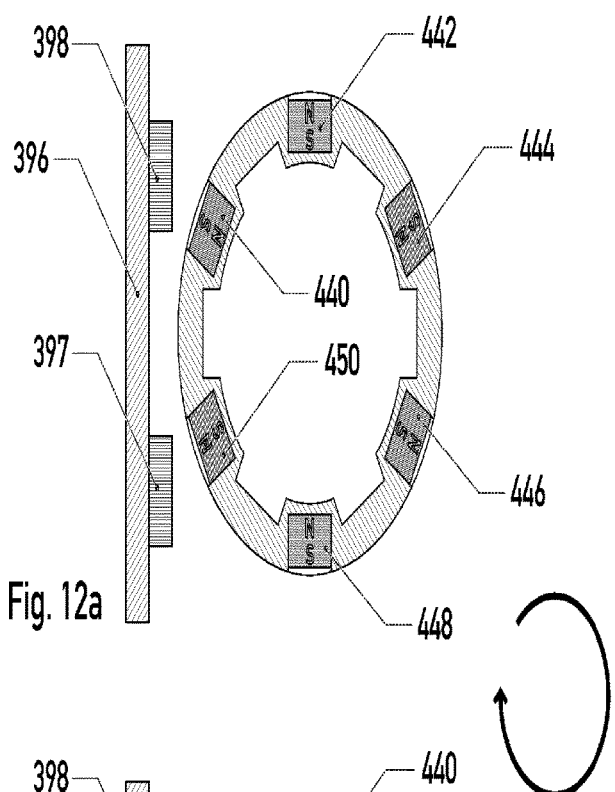
Figure 12B:
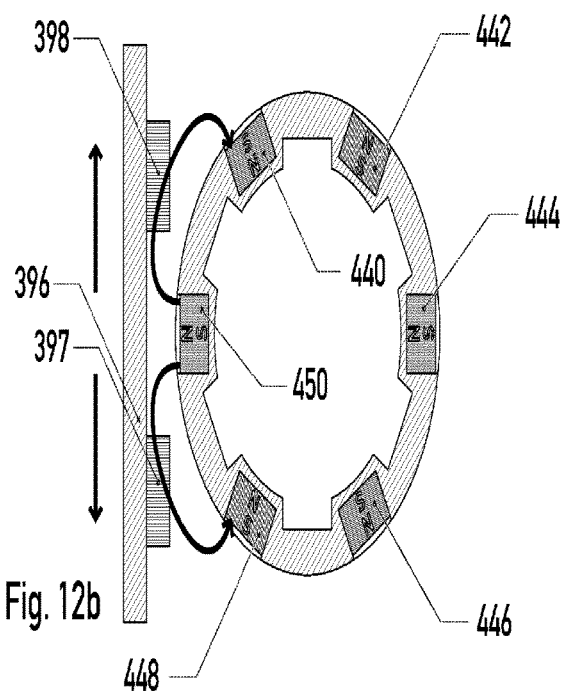

In FIG. 12b the magnetic sensor 397 is penetrated by a magnetic field between magnets 440 and 442. The magnetic field is oriented from top to bottom in the Figure. The magnetic sensor detects a signal that is assigned to zero. The magnetic sensor 398 is penetrated by a magnetic field between the magnets 450 and 440. In the drawing the magnetic field is oriented from bottom to top. The magnetic sensor detects a signal that is assigned to one.

Figure 12C:
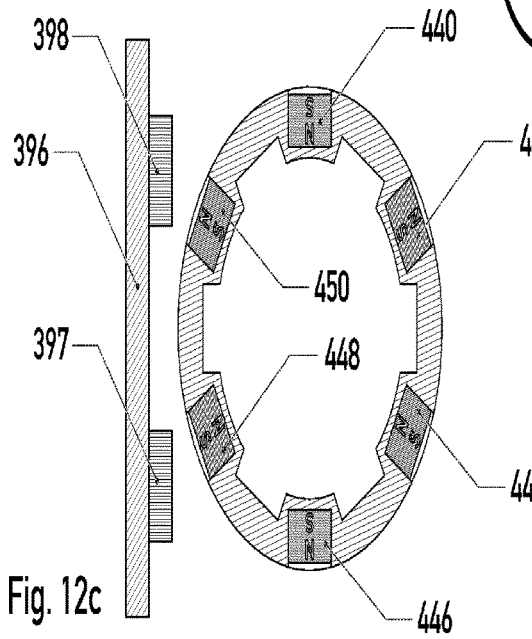

In FIG. 12c the magnetic fields are undefined. The sensors keep the previous signal. Upon further clockwise rotation the directions of the magnetic field in both magnetic sensors 397 and 398 are reversed. This is shown in FIG. 12d.

The output signals of the magnetic sensors 397 and 398 change. The orientation of the magnetic fields and hence their output signal changes with every rotation by 60°. The sequence of the changes are electronically processed and converted into adjusted units which then are displayed on the display 382. For illustration the following table is shown:

| clockwise | magnetic sensor | magnetic field direction | output signal |
| --- | --- | --- | --- |
| FIG. 12b | magnetic sensor 397 | down | 0 |
|  | magnetic sensor 398 | up | 1 |

Figure 12D:
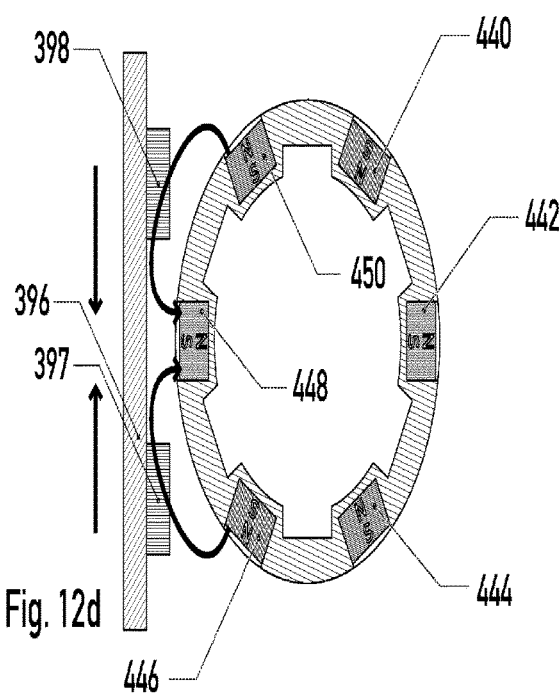

| | clockwise | magnetic sensor | magnetic field direction | output signal |
|---|---|---|---|---|
| FIG. 12c | | magnetic sensor 397 | | 0 |
| | | magnetic sensor 398 | | 1 |
| FIG. 12d | | magnetic sensor 397 | up | 0 |
| | | magnetic sensor 398 | down | 1 |
| FIG. 12a | | magnetic sensor 397 | | 0 |
| | | magnetic sensor 398 | | 1 |

The counting in the other rotating direction operates likewise. It is possible to use Hall sensors. Contrary to mechanical parts for processing the adjusted dosage the components of the present embodiment do not wear off. Hence, the accuracy and the life time of the application assembly 300 are further improved.

The pressure spring 418 is clamped between the coupling element 422 and the ring magnet 416. The cap side of the block 414 is provided with a broadened edge 452 with the ring magnet 416 and dose setting knob sided a smaller end. A ledge 456 is formed between the smaller end 454 and the broadened end 452. The smaller end 454 is hidden in the counter crown 408 up to the ledge 456.

The counter crown 408 is attached to the dose setting knob 402. Guiding grooves 460 are provided in the counter crown 408. Such grooves do not break through the cap end 462. Corresponding guiding rails 464 of the shaft 420 run in the guiding grooves. The shaft 420 is biased by a balance spring 410 between shaft 420 and doses setting knob 402. The securing ring 412 limits the path of the guiding rails 464 in the guiding grooves 460. The balance spring 410 ensures that the nut 420 is reliably pressed against the casing 328.

The dose setting knob 402 can be hidden in the knob enclosure 400. In the hidden position the pressure spring 418 is biased. In its extended position the pressure spring is relaxed. Thus, the shaft 420 is slightly pushed off the coupling element 422. A gap appears between the nut 340 and the shaft 420.

Upon rotation of the dose setting knob 402 the counter crown 408 connected thereto is rotated. The rotation is transmitted onto the shaft 420 through the guiding grooves 460 and the guiding rails 464. By a rotation of the dose setting knob 402 the shaft 420 is also rotated in a clockwise direction. Thereby, the nut 340 is moved in the coupling element 422 in the direction of the shaft 420. The gap between the shaft 420 and the nut 340 is reduced. The gap between the casing 328 and the nut 340 is increased.

By pressing the dose setting knob in the direction of the cap the shaft 420 is moved and the pressure spring 418 is compressed. The gap between shaft 420 and nut 340 is reduced. Upon continuous pressure on the shaft 420 the nut moves in the direction of the cap as soon as the shaft touches nut. As the nut 340 is attached to the threaded rod by the thread it is also moved. The movement ends, once the gap between nut 340 and casing 328 is closed. Only the pressure spring 418 is compressed thereafter.

Thereby, the ring magnet 416 is moved until it triggers the ON sensor 399. In the present embodiments the ON sensor comprises a reed contact. The ON sensor generates a signal indicating that insulin has been administered. It also serves for switching the application assembly 300 on and off.

The crown 408 is provided with a tooth shaped structure 466 at its dose setting knob end 402. Along the outside of the crown 408 four circumferential guiding rails 468 are provided. A ring shaped projection 470 interconnects the guiding rails 468 of the crown 408. The dose setting knob side of the ring shaped projection is provided with a tooth shaped wave track. The tooth shaped wave track is broken by the guiding rails 468. The dose setting knob end of the guiding rails 468 matches the tooth shaped structure 466.

A push sleeve 474 which is provided with a tooth shaped structure 476 is attached in the dose setting knob 402. The tooth shaped structure 476 and the tooth shaped structure 466 form a spur gear. Projections 478 are provided at the outer wall of the push sleeve 474. They correspond to the guiding rails 468 of the crown 408.

The hat element 404 is pivotably mounted in the back portion of the casing 316. For this purpose the hat element 404 is provided with a circumferential brim on its outside. Corresponding to the brim a circular groove 482 is provided in the knob enclosure 400. Brim and circular groove 482 form a bush bearing.

The hat element is provided with guiding grooves 488. The number of the guiding grooves 488 matches the number of projections 478 of the push sleeve 474 and the number of guiding rails 468 of the counter crown 408. The push sleeve 474 is axially movable in the hat element 404.

The cap end of the hat element 404 with the brim is provided with a saw tooth shaped spur gear 486 on the inner edge that engages with the ends of the guiding rails 468. The saw teeth of the spur gear 486 of the hat element 402 are designed in such a way that a guiding groove 488 is arranged after every second steep flank.

The spring constant of the balance spring 410 is larger than the spring constant of the pressure spring 418.

In OFF mode of the application assembly 300 the dose setting knob 402 is hidden in the knob enclosure 400. The dose setting knob 402 is secured against accidental actuation. A circumferential ledge on the inside of the crown 406 and a thickened portion provided at the end 462 of the counter crown prevent its slipping out of the dose setting knob 402.

For release the dose setting knob 402 is pushed in the direction of the cap. Thereby, the push sleeve 474 pushes the crown 406 so far in the direction of the cap that the guiding rails 468 of the crown 406 are pushed over the steep flank of the saw tooth shaped spur gear 486 of the hat element 404. By effect of the spur gear between push sleeve 474 and crown 406 the crown 406 is turned further by one saw tooth of the hat element 404. Now guiding rails 468 face corresponding guiding grooves of the hat element 404.

By releasing the dose setting knob 402 the crown 406 moves towards the knob enclosure 400 by means of the spring pressure of the pressure spring 418. Thereby, the dose setting knob 402 moves out of the knob enclosure 400. The dose setting knob is now accessible and can be rotated and actuated.

After adjusting the dosage the crown 406 is pushed in the direction of the cap by pushing the dose setting knob 402. Thereby, the shaft 420 is also moved. The shaft 420 actuates the nut 340 that transmits its movement to the threaded rod 338. The threaded rod 338 pushes the plug of the cartridge to administer insulin. The ring magnet 416 moves towards the cap, whereby the administered insulin dosage is saved. A time stamp is generated. This time stamp is filed in a memory. The insulin pen is shifted into an energy saving mode where the display is turned off.

As soon as the nut 340 touches the casing 328 the pressure spring 418 is further compressed upon pushing the dose setting knob 402 and the crown 406 moves further in the direction of the cap. When the guiding rails 468 of the crown 406 are not guided by the guiding grooves 488 of the hat element 404 anymore the crown is turned further by one saw tooth of the hat element 404 by effect of the spur gear between push sleeve 474 and crown 406. There are no guiding grooves corresponding to the guiding rails 468 of the crown 406.

If the dose setting knob is not pushed anymore the pressure spring 418 relaxes and pushes the crown 406 against the hat element 404. The crown 406 is locked. In this position the dose setting knob 402 is concealed in the casing of the application assembly 300. The dose setting knob 402 is secured against accidental actuation.

The application assembly 300 is provided with the same electronic options as the assembly 10.

What is claimed is:

1. A replaceable adapter assembly being adapted and configured to be used in a device for the administration of a selected dosage of insulin or other medicaments from a cartridge, the device comprising a housing with a removable front portion and the claimed replaceable adapter assembly comprises:
   (a) a cartridge with a moveable plug guided in said cartridge,
   (b) a first threaded element formed by a threaded rod with an external, male thread and a thread lead, movable in a first direction to move the plug; and
   (c) a casing having an open side for receiving the cartridge and which is provided with an aperture at its opposite end for guiding said threaded rod in a rotationally secured way, and
   (d) a second threaded element formed by a nut and threaded with a thread lead matching the thread lead of the threaded rod for adjusting a dose, pivotably screwed to said threaded rod outside of said casing and limiting movement of said threaded rod in the first direction, and wherein
   (d) the first and the second threaded element are integral parts of the replaceable adapter assembly and said thread lead of said first element and said thread lead of said second threaded element are adapted to the dimension and/or the content of said cartridge,
   and wherein said first and second threaded elements of said replaceable adapter assembly correspond to an opening of said housing of the device so as to be frontally insertable into the housing, and wherein an outer surface of said case of the replaceable adapter assembly corresponds to an inner surface of said front portion of the housing so that the replaceable adapter assembly is securable in its position by connecting the front portion to the housing.

2. An assembly for the administration of a selected dosage of insulin or other medicaments from a cartridge by moving a plug guided in said cartridge, comprising a replaceable adapter assembly for the reception of the cartridge, the adapter assembly comprising:
   (a) a first threaded element formed by a threaded rod with an external, male thread and a thread lead, movable in a first direction to move the plug; and
   (b) a casing having an open side for receiving a cartridge and which is provided with an aperture at its opposite end for guiding said threaded rod in a rotationally secured way, and
   (c) a second threaded element formed by a nut and threaded with a thread lead matching the thread lead of the threaded rod for adjusting a dose, pivotably screwed to said threaded rod outside of said casing and limiting movement of said threaded rod in the first direction, and wherein
   (d) the first and the second threaded element are integral parts of the adapter assembly and said thread lead of said first element and said thread lead of said second threaded element are adapted to the dimension and/or the content of said cartridge, and
   wherein the assembly further comprises a sensor assembly for contactless sensing a selected and/or administered dosage, wherein the sensor assembly comprises:
   (a) one or more magnets on one of the rotating components for adjusting the dosage,
   (b) one or more magnetic sensors detecting a rotation of said magnets,
   (c) a ring magnet and an ON-sensor with the ring magnet being adapted to move relatively to the ON-sensor so as to trigger the ON-sensor when the dosage is administered and with the ON-sensor being adapted to generate a signal indicating that the dosage has been administered, and
   (d) processing and display means for processing and/or displaying a dosage corresponding to a detected movement determined from said detected rotation and/or for saving the administered dose,
   wherein the one or more magnetic sensors internally do not comprise any mechanically moveable parts.

* * * * *